United States Patent [19]

David-Comte

[11] Patent Number: 5,688,956
[45] Date of Patent: Nov. 18, 1997

[54] METHOD FOR PREPARING N-METHYL 2-(3-PYRIDYL) (1R,2R)-2-TETRAHYDROTHIO-PYRANCARBOTHIOAMIDE-1-OXIDE

[75] Inventor: Marie-Thérèse David-Comte, Villemoisson-su-Orge, France

[73] Assignee: Rhone-Poulenc Rorer S.A., Antony Cedex, France

[21] Appl. No.: 515,421

[22] Filed: Aug. 15, 1995

Related U.S. Application Data

[63] Continuation-in-part of PCT/FR94/00221, Feb. 28, 1994

[30] Foreign Application Priority Data

Mar. 2, 1993 [FR] France ............... 93 02369

[51] Int. Cl.$^6$ ............... C07D 401/04
[52] U.S. Cl. ............... 546/280.1
[58] Field of Search ............... 546/280.1

[56] References Cited

U.S. PATENT DOCUMENTS 5,053,415  10/1991  Brewster et al. ............ 514/336
5,120,852  6/1992   Aloup et al. .

OTHER PUBLICATIONS

Univ. of Notre Dame Press, 1972 (pp. 24–28, 32), Wilen, Tables of Resolving Agents and Optical Resolutions, English Original.

J. Med. Chem., vol. 35, No. 20 (1992) pp. 3613–3624, Brown, Chapman, Cook, Hart, McLay, Jordan et al., Synthesis and biological Activity of trans-(+/-)-N-Methyl-2-(3pyri, English Original.

*Primary Examiner*—Jane Fan
*Attorney, Agent, or Firm*—Raymond S. Parker, III; Paul R. Darkes; Martin F. Savitzky

[57] ABSTRACT

The present invention relates to a process for the preparation of (1R,2R)-N-methyl -2-(3-pyridyl)tetrahydrothiopyran-2-carbothioamide 1-oxide of formula:

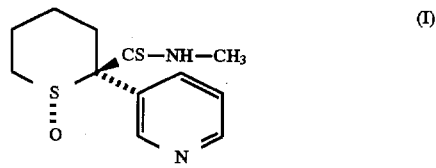

(I)

which is particularly useful as an antihypertensive and as a cardioprotective agent.

8 Claims, No Drawings

METHOD FOR PREPARING N-METHYL 2-(3-PYRIDYL) (1R,2R)-2-TETRAHYDROTHIO-PYRANCARBOTHIOAMIDE-1-OXIDE

This application is a continuation-in-part of co-pending PCT Serial No. FR94/00221, filed Feb. 28, 1994, designating the United States.

BACKGROUND OF THE INVENTION

1. Field of the Invention

The present invention relates to a process for the preparation of (1R,2R)-N-methyl -2-(3-pyridyl) tetrahydrothiopyran-2-carbothioamide 1-oxide of formula:

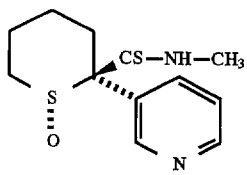

(I)

which is particularly useful as an antihypertensive and as a cardioprotective agent.

2. Reported Developments

European Patent EP 0,097,584 has described thioamide derivatives of general formula:

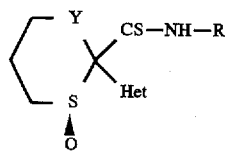

(II)

in which R represents a hydrogen atom or an alkyl radical containing 1 to 4 carbon atoms, Het represents a heterocyclic radical of aromatic character and Y represents a valency bond or a methylene radical.

The presence of two asymmetric centres leads to 4 stereoisomers which may optionally be separated into two cis and trans racemic pairs.

The product of general formula (II) for which R represents a methyl radical, Het represents a 3-pyridyl radical and Y represents a methylene group, in the form of the trans racemic mixture which may be represented in the following way:

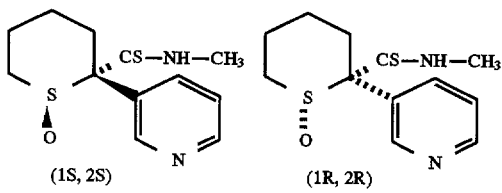

(1S, 2S)  (1R, 2R)

is valuable as an antihypertensive (EP-0,097,584) and, particularly the (1R,2R) isomer, as a cardioprotective agent (EP-0,429,324) at doses for which the antihypertensive effect is not exhibited.

(1 R,2R)-N-Methyl-2-(3-pyridyl)tetrahydro-thiopyran-2-carbothioamide 1-oxide may be isolated from a mixture of the (1R,2R) and (1 S,2S) forms, in particular from the racemic mixture, by chiral-phase chromatography (EP-0,097,584), or may be prepared by stereoselective methods (EP-0,426,557). These processes make it necessary to use large quantities of solvents or else to perform a large number of steps.

SUMMARY OF THE INVENTION

The subject of the present invention is directed to (1R,2R)-N-methyl-2-(3-pyridyl) tetrahydropyran-2-carbothioamide 1-oxide from a salt of the mixture of (1R,2R)- and (1S,2S)-trans isomers, and in particular from the racemic mixture, with an optically active acid.

DETAILED DESCRIPTION

More particularly, the process according to the invention consists in selectively precipitating a salt of the (1R,2R)-trans isomer with an optically active acid in a suitable solvent, and then in liberating the (1R,2R)-trans isomer from its salt.

For the implementation of the process according to the invention, it is particularly advantageous to use an optically active acid chosen from (−)-camphanic acid and (+)-3-bromo-10-camphorsulphonic acid.

The solvents which are particularly suitable for the selective crystallization of the salt of the (1R,2R)-trans isomer with an optically active acid are preferably chosen from water, aliphatic alcohols containing 1 to 4 carbon atoms such as methanol, ethanol or isopropanol, and aqueous-alcoholic mixtures.

(1 R,2R)-N-Methyl-2-(3-pyridyl)tetrahydrothiopyran-2-carbothioamide 1-oxide is liberated from its salt by means of an inorganic or organic base, the procedure being carried out in water or in a mixture consisting of water and an immiscible solvent in which the (1R,2R)-trans isomer is soluble. Alkali metal carbonates or hydroxides (sodium hydroxide, potassium hydroxide or sodium carbonate) are preferably used as inorganic base. Tertiary aliphatic amines (triethylamine) or pyridine, whose basicity is sufficiently great to liberate the optically active acid from its salt, may be used as organic base. Preferably, potassium hydroxide is used in an aqueous-organic medium such as a water/halogenated aliphatic hydrocarbon mixture such as water/methylene chloride: in this way, the (1R,2R)-trans isomer dissolves in the organic solvent as it is being formed, with the salt of the optically active acid remaining in aqueous solution.

(1 R,2R)-N-Methyl-2-(3-pyridyl)tetrahydrothiopyran-2-carbothioamide 1-oxide is separated from its solution according to the usual methods and it may be purified according to known techniques, for example by crystallization.

The mixture of the (1R,2R)- and (1S,2S)-trans isomers of N-methyl-2-(3-pyridyl) tetrahydrothiopyran-2-carbothioamide 1-oxide, and more particularly the racemic mixture, may be prepared under the conditions described in European Patent EP-0,097,584.

The examples which follow illustrate the present invention.

EXAMPLE 1

1900 cm³ of ethanol, 165 g of the trans racemic mixture of N-methyl-2-(3-pyridyl) tetrahydrothiopyran-2-carbothioamide 1-oxide and 121.9 g of (−)-camphanic acid are introduced into a 2-liter reactor. The suspension is heated to 65° C. until complete dissolution is obtained. After cooling to 45° C., crystallization is initiated with 100 mg of the salt of (1R,2R)-N-methyl-2-(3-pyridyl) tetrahydrothiopyran-2-carbothothiomide 1-oxide with (−)-camphanic acid. The suspension is cooled over a period of 2 hours to a temperature in the region of 20° C. and then stirred for 30 minutes at this temperature. The crystals are separated off by filtration, then washed with twice 150 cm³ of ethanol and finally dried under reduced pressure at 40° C. 95.76 g of a white powder containing 57.7% of (1R,2R)-N- methyl-2-(3-pyridyl)tetrahydrothiopyran-2-carbothioamide 1-oxide are thus obtained.

The enantiomeric excess is in the region of 100%.

The yield is 33.4%.

EXAMPLE 2

940 cm$^3$ of methylene chloride, 188 g of the salt of (1R,2R)-N-methyl -2-(3-pyridyl)tetrahydrothiopyran-2-carbothioamide 1-oxide with (−)-camphanic acid and 880 cm$^3$ of demineralized water are introduced into a 2-liter reactor. To the stirred suspension are added 68.6 g of 30% (w/w) aqueous potassium hydroxide solution over a period of 10 minutes. Stirring is carried out for 15 minutes. After settling has taken place, the organic phase is separated off and washed with 188 cm$^3$ of distilled water and then dried. After evaporation of the solvent, 90.5 g of pure (1R,2R)-N-methyl-2-(3-pyridyl) tetrahydrothiopyran-2-carbothioamide 1-oxide are obtained, with a yield of 83.7%.

The enantiomeric excess is in the region of 100%.

I claim:

1. Process for the preparation of (1R,2R)-N-methyl-2-(3-pyridyl) tetrahydrothiopyran-2-carbo-thioamide 1-oxide of formula:

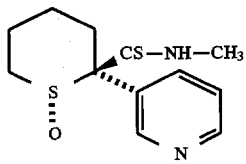

wherein a salt of (1 R,2R)-N-methyl-2-(3-pyridyl) tetrahydro-thiopyran-2-carbothioamide 1-oxide with an optically active acid chosen from (−)-camphanic acid and (+)-3-bromo-10-camphorsulphonic acid is selectively precipitated in a solvent chosen from water, aliphatic alcohols containing 1 to 4 carbon atoms and aqueous-alcoholic mixtures, from the salt of a mixture of the (1R,2R)- and (1S,2S)-trans isomers of N-methyl-2-(3-pyridyl) tetrahydrothiopyran-2-carbothioamide 1-oxide with the optically active acid, and the (1R,2R)-N-methyl-2-(3-pyridyl)tetrahydrothiopyran-2-carbothiodiamine 1-oxide is then liberated from its salt.

2. Process according to claim 1, wherein the solvent is chosen from methanol, ethanol and isopropanol.

3. Process according to claim 1, wherein the liberation of (1R,2R)-N-methyl-2-(3-pyridyl)tetrahydrothiopyran-2-carbothioamide 1-oxide from its salt with the optically active acid is carried out by means of an inorganic or organic base.

4. Process according to claim 3, wherein the procedure is carried out in water or in a mixture of water and an immiscible organic solvent in which (1R,2R)-N-methyl-2-(3-pyridyl)tetrahydrothiopyran-2-carbothioamide 1-oxide is soluble.

5. Process according to claim 3, wherein the inorganic base is chosen from alkali metal carbonates and hydroxides.

6. Process according to claim 5, wherein the inorganic base is potassium hydroxide.

7. Process according to claim 3, wherein the organic base is chosen from tertiary aliphatic amines and pyridine.

8. Process according to claim 4, wherein the procedure is carried out in a mixture of water and a halogenated aliphatic hydrocarbon.

* * * * *